United States Patent [19]

Bauer et al.

[11] Patent Number: 4,777,047

[45] Date of Patent: Oct. 11, 1988

[54] TRANSDERMAL APPLICATION FORM OF CALCIUM ANTAGONISTS

[75] Inventors: Kurt H. Bauer, Freiburg; Dittmar Quade, Gundelfingen, both of Fed. Rep. of Germany; Majid Mahjour, Morris Plains, N.J.

[73] Assignee: Godecke Akt., Berlin, Fed. Rep. of Germany

[21] Appl. No.: 903,339

[22] Filed: Sep. 3, 1986

[30] Foreign Application Priority Data

Sep. 4, 1985 [DE] Fed. Rep. of Germany ....... 3531545

[51] Int. Cl.$^4$ ............................................... A61K 13/00
[52] U.S. Cl. ................... 424/449; 424/445; 424/448
[58] Field of Search ................................ 424/448, 449

[56] References Cited

U.S. PATENT DOCUMENTS 4,637,930  1/1987  Konno et al. .......... 424/449
4,685,911  8/1987  Konno et al. .......... 424/449

FOREIGN PATENT DOCUMENTS 152281    8/1985  European Pat. Off. .
189861    8/1986  European Pat. Off. .
59-175415 4/1984  Japan .

OTHER PUBLICATIONS

Journal of Pharmaceutical Sciences, 8/84, E. R. Cooper; "Increased Skin Permeability for Lipophilic Molecules".
Chemical Abstracts, vol. 96, 2/82; Seite 378, Ref. No. 40902j, Taisho Pharm. Co. Ltd., JPA 81110614.

*Primary Examiner*—Thurman K. Page
*Assistant Examiner*—L. R. Horne
*Attorney, Agent, or Firm*—Elizabeth M. Anderson

[57] ABSTRACT

The use of permeation enhancers permits the formulation of transdermal dosage forms for calcium antagonists. These dosage forms are administrable to humans and other mammals, e.g., bovines.

5 Claims, No Drawings

TRANSDERMAL APPLICATION FORM OF CALCIUM ANTAGONISTS

DESCRIPTION

Calcium antagonists represent important active substances for the prevention and treatment of coronary heart diseases and of peripheral bloodflow disturbances. Due to the fact that they undergo relatively extensive first pass metabolism, however, only a relatively small portion of the active substance becomes effective upon peroral administration, which necessitates that correspondingly higher dosages must be provided to yield the bioavailability required. The peroral bioavailability of, for instance, diltiazem is in the order of 40 to 60 percent. As a rule, parenteral application can only be carried out by properly trained personnel, thus excluding self-medication by the patient. It was also possible to realize transdermal forms of application in the case of certain active substances, principally those agents that have a very small molecular size, display a polar structure and are active in the range below 5 mg/dose. Hence, most recently, so-called nitrate patches were developed for the treatment of angina pectoris, in which a sufficient quantity of active substances of approx. 1 mg/dosage/day of nitroglycerin is able to permeate the skin. Similarly small quantities of clonidine, the potent antihypertensive and diuretic agent, can be effectively applied transdermally.

Except for first pass metabolism, calcium antagonists require—as a rule—comparatively high dosages (factor 10 to 100) and cannot be compared to nitroglycerin or clonidine in terms of their molecular size. As for their structure they can, as a whole, hardly be termed polar, exhibiting, in a certain sense, rather a predominantly symmetrical structure.

Surprisingly it was nevertheless found that in solution, with the aid of skin permeation enhancers, they are able upon percutaneous application, to yield adequate blood levels and to maintain these over a period of at least 24 hours.

The present invention is, therefore, concerned with transdermal application forms for mammals, containing at least one calcium antagonist as active substance and the usual excipient and adjuvant substances.

Such percutaneous application forms have the great advantage of being able—in contrast to peroral application forms or, eg., injectable forms—to maintain constant blood level without—fluctuations over long periods of time. Moreover, as already mentioned, there is no first pass metabolism upon percutaneous application. In addition, application e.g. in the form of a correspondingly impregnated patch, is very simple to carry out and has to be performed only once per day.

Pertinent transdermal application forms can be prepared analogously to the known nitrate patches, eg., by immersing adequately sized (10 to 50 cm$^2$, preferably approx. 25 to 35 cm$^2$) patches in a solution of the active substance, which should preferably also contain spreading or surface-active adjuvants, such as isopropyl myristate, PEG 6-capric acid, caprylic acid glyceride, or ethyl oleate. The calcium antagonists mentioned below should be applied in the form of their free bases since salt forms, as is generally acknowledged, are generally unable to penetrate the skin and since all of the following calcium antagonists contain amino groups.

The following substances, amongst others, come into consideration as calcium antagonists: verapamil, gallopamil nifedipine, niludipine, nimodipine, nicardipine, prenylamine, fendiline, terodiline, nisaldipine, nitrendipine, and perhexiline, in particular and preferably, however, diltiazem. Combinations are contemplated.

The oral dose of diltiazem is 180 mg daily. The fact that equivalent blood levels can be obtained upon transdermal application, must be regarded as extremely surprising.

The efficacy of the new application form has so far been tested on hairless mice as well as on pigs. Its efficacy was confirmed in both types of animals. Moreover, the efficacy demonstrated on pigs shows that, in addition to its employment in humans, the new form could be used very effectively in veterinary medicine as well.

It is known of course that breeding pigs are under great stress when they are being transported or are placed in unfamiliar surroundings. The effects of stress caused by travelling are particularly bad when the animals are being transported in large numbers, without the space for movement they naturally require, in narrow boxes.

Boars at the time of copulation and valuable breeding pigs at agricultural exhibitions are also under extreme stress. Up until now an attempt has been made to reduce the degree of stress by using tranquilizers to directly influence the central nervous system. This measure certainly helps to keep a limit on the high death quotas due to shock but, on the other hand, results in the animals becoming sleepy and sluggish so that boars are unable to successfully perform the copulatory act and breeding pigs present rather a sad sight at exhibitions.

On the other hand, pigs intended for slaughter are admittedly calmed down by comparatively large doses of tranquilizers, though the animals are only allowed to be slaughtered after a fixed period of time following administration of the medicament has elapsed in order to ensure that the meat obtained no longer contains an undesirable level of medicament in the tissues.

All this demonstrates that the use of tranquilizers has until now admittedly been necessary but is also accompanied by a number of unavoidable drawbacks.

The application form in accordance with the present invention allows for the protection of mammals from the undesired consequences of subjection to unavoidable stress.

Moreover, up until now the use of calcium antagonists to reduce excess stress on animals, particularly pigs, has been completely unknown.

The use of calcium antagonists in this way ensures that pigs, for example, no longer collapse even under very high stress conditions. Thus, it has been ascertained that the death of the animals is, as a rule, to be attributed not to the effects of shock but rather to a partial destruction of heart muscle tissue resulting from an unnaturally high heart rate due to the action of stress and the resultant $O_2$-imbalance.

Contrary, therefore, to what has previously been assumed to be self-evident by specialist circles, it is not a question of reducing the nervous tension of the animals by means of tranquilizing drugs; rather it is the case that the animals can survive with surprising ease the stress previously regarded as being an unavoidable danger when provision is made to economize the blood flow through the heart muscle tissue. A depression of the central nervous system is thus unnecessary.

Consequently, a further object of the present invention is the use of calcium antagonists, especially diltiazem, for the management of damage to domestic animals brought about by stress.

When used for this purpose the actual route of administration is not particularly important, provided that care is taken to ensure that a sufficiently high tissue level (about 50 to 100 ng/ml) is achieved and that the absorption by the animals takes place as quickly as possible.

In principle, therefore, both administration by injection (preferably by the intramuscular route) and oral administration can be used, provided that one is ready to accept the drawbacks of the latter forms. In the case of intramuscular injection, approx. 0.8 to 0.9 mg of the active substance per kg of body weight are preferably to be used.

For peroral forms, which can be added to the feed or drinking water, correspondingly higher dosages of about 1.7 to 1.9 mg/kg of body weight are to be used.

The results of numerous experiments have shown that for administration to animals, especially in the case of domestic pigs, the transdermal form (applied at the pig's ear) in accordance with the present invention is especially suitable, since it is easy to employ and gives a reproducible, rapid and high therapeutic activity level.

For this form of administration, the calcium antagonist used as active substance is dissolved or suspended in a neutral carrier substance and applied in this form over a relatively large surface area to the outer skin of the pig's ear. Surprisingly, within relatively few minutes (15 to 20 minutes), a sufficient tissue level is achieved.

Since calcium antagonists, in contrast to tranquilizers, such as chlorpromazine or those of the azepam type of compounds, have a very short half life, an inadmissible build up of the active substance in the tissues of the slaughtered animal's meat can be avoided without any problems. In particular, the waiting times are thereby drastically reduced.

In addition, the transdermal form of administration is especially easy to vary. If, for example, in the case of pigs, it is necessary to maintain the therapeutic activity level at a desired level, not just for a short time but also for a comparatively long period of time, then it is possible to fix a pharmacotechnological composition in a reservoir packing on the pig's ear. The active substance can then penetrate through the skin over a comparatively long period of time and the animal is afforded around-the-clock protection from the possibly fatal effects of stress arising, for example, during transfer to another sty, transportation or copulation.

The transdermal form of administration is therefore particularly suitable for pigs.

A further object of the present invention is thus a transdermal form of administration for mammals principally humans, which contains at least one calcium antagonist and conventional adjuvant and additive materials. Diltiazem is preferred as the active substance.

For solid calcium antagonists to be administered orally, conventional adjuvant and filler materials can be used.

These forms of application can contain conventional excipients, lubricants, and disintegration additives. Such additives include, for example, tartrate and citrate buffers, ethanol, complex formers (such as ethylendiaminetetraacetic acid and non-toxic salts thereof) as well as polymers (such as liquid polyethylene oxide) for the regulation of viscosity and the like.

Solid carrier substance include, for example, starch, lactose, mannitol, methyl cellulose, talc, highly dispersed silic acid, high molecular weight fatty acids (such as stearic acid), gelatine, agar-agar, calcium phosphate, magnesium stearate, animal and vegetable fats and solid polymers (such as polyethylene glycol).

Water is normally used as the injection solution; accordingly it contains the additives usual in the case of injection solutions, such as stabilizing agents, solubilizing agents and/or buffers.

The transdermal forms of application preferably contain organic solvents with a good skin compatibility, such as ethanol, methylpyrrolidone, polyethylene glycol, oleyl alcohol, octanol, linoleic acid, triacetin, propylene glycol, glycerol, solketal, or dimethyl sulfoxide, which facilitate the penetration through the skin. Mixtures are operable.

In order to produce evidence for the efficacy of the transdermal preparation forms, the following experiments were carried out:

The permeability of diltiazem through the skin of hairless mice was investigated.

3 g of diltiazem hydrochloride were dissolved in 30 ml distilled water. Ammonium hydroxide was added dropwise thereto to precipitate the base. The base was extracted with 3 times 20 ml of methylene chloride. The methylene chloride fraction was dried by the addition of anhydrous sodium sulfate. Following evaporation of the solvent, the base was obtained in the form of crystals.

In order to conduct the experiments, skin sections were taken from five to seven-week old hairless mice. The sections were mounted on conventional diffusion cells in such a way that the stratum corneum was facing the donor liquid.

To remove extraneous debris, the dermal side of the skin was in contact with saline for two hours. This was then replaced by a solution containing diltiazem. The receiver solution consisted—in the case of low flux formulations—of saline, or in the case of formulations with high fluxes—of isotonic citrate phosphate buffer (pH 4.5).

After removal of a certain volume of the liquid at timed intervals the receiver solution was monitored for its content of diltiazem. The quantity of liquid withdrawn was replaced by fresh solution. Prior to the determination of the drug concentration by high pressure liquid chromatography the solution was filtered through a 0.45 nylon filter. The test temperature was 37° C.

Assuming the flux of human skin is five times lower than the flux of mouse skin, the flux values determined must be provided with a factor of 0.2 to below an inference to be made on the permeability of human skin.

The following TABLE I contains the flux values and permeability values determined from the various solvent systems used. The flux values express the quantity diffused under the test conditions stated via a skin surface of 1 $cm^2$ during one hour from the donor to the acceptor side. The lag time is the time from the start of the experiment up until the steady state flux is attained.

The following solvents were investigated:
(1) Octanol (OC)
(2) Propylene glycol (PG)
(3) Oleyl alcohol (OA)
(4) Linoleic acid (LA)
(5) Triacetin (TA)

The ratios stated refer to the weight

TABLE I

| Vehicle | Donor-Concentration (mg/ml) | Flux (ug/cm²) | Lag Time (hours) | Permeability (cm/sec × 10⁷) |
|---|---|---|---|---|
| OC:PG 20:80 | 52.42 | 149.27 | 5.2 | 7.9 |
| OA:PG 20:80 | 45.75 | 83.71 | 0.82 | 5.1 |
| LA:PG 2,5:97,5 | 62.84 | 610.5 | 15.4 | 27.0 |
| LA:PG 5:95 | 75.37 | 555.09 | 14.5 | 20.5 |
| LA:PG 10:90 | 83.24 | 687.64 | 12.5 | 22.9 |
| LA:PG 20:80 (solution) | 126.46 | 165.32 | 4.0 | 3.6 |
| LA:PG:TA 20:30:50 | 90.64 | 231.54 | 15.2 | 7.1 |

It can be seen from Table I that LA:PG mixtures with an excess of PG yielded particularly high flux values, preferred is a relationship of 1 to 20 weight % LA and 99 to 80 weight % PG.

In the case of the best flux value obtained (LA:PG, 10:90) of 687,64, the following quantity of activity would be absorbed by 30 cm² of human skin within a period of 24 hours after steady state:

$$\frac{687,64 \times 30 \times 24}{1000 \times 5} = 99.02 \text{ mg}$$

Taking into consideration the absence of first pass metabolism, this corresponds to an oral dose of approx. 180 to 200 mg diltiazem.

The following examples serve to illustrate the present invention in more detail:

EXAMPLE 1

A solution is prepared from 0.5 mg diltiazem base, 2.0 ml isopropyl myristate and 10.0 ml ethanol. 2.0 ml of this solution is spread over the entire outer surface of a pig's ear, the pig weighing 40 kg. After only 25 minutes, a diltiazem plasma level of 90 ng/ml can be ascertained, which after 60 minutes decreases to 30 ng/ml.

EXAMPLE 2

A mixture is prepared from 10 g linoleic acid and 90 g propylene glycol. 8.324 g diltiazem base are dissolved in this mixture. Gauze squares with a surface of 30 cm² (i.e. with sides of 5.5 cm length) which have been coated with plastic on one side are immersed in the mixture obtained. The squares are then sealed, into aluminium foil.

What is claimed is:

1. Transdermal pharmaceutical form of administration for mammals containing diltiazem as active ingredient and solvents linoleic acid and propylene glycol and additive materials.

2. Transdermal form according to claim 1, wherein linoleic acid and propyleneglycol are present in a relationship of 1-20 weight % acid and 99 to 80 weight % glycol.

3. Transdermal pharmaceutical form according to claim 1 wherein said mammal is a pig.

4. Transdermal pharmaceutical form according to claim 1, consisting of gauze squares impregnated with a solution of diltiazem in a mixture of 10 parts by weight linoleic acid and 90 parts by weight propyleneglycol.

5. Transdermal pharmaceutical form according to claim 1, wherein said mammal is a human being.

* * * * *